US010860617B2

(12) United States Patent
Yagami et al.

(10) Patent No.: US 10,860,617 B2
(45) Date of Patent: Dec. 8, 2020

(54) INFORMATION PROCESSING APPARATUS, INFORMATION PROCESSING METHOD, AND PROGRAM

(71) Applicant: SONY CORPORATION, Tokyo (JP)

(72) Inventors: Kishin Yagami, Tokyo (JP); Hisahiro Suganuma, Tokyo (JP); Mitsuru Takehara, Tokyo (JP); Yuichi Kageyama, Tokyo (JP)

(73) Assignee: SONY CORPORATION, Tokyo (JP)

( * ) Notice: Subject to any disclaimer, the term of this patent is extended or adjusted under 35 U.S.C. 154(b) by 679 days.

(21) Appl. No.: 15/317,938

(22) PCT Filed: Mar. 17, 2015

(86) PCT No.: PCT/JP2015/057944
§ 371 (c)(1),
(2) Date: Dec. 9, 2016

(87) PCT Pub. No.: WO2015/198652
PCT Pub. Date: Dec. 30, 2015

(65) Prior Publication Data
US 2017/0116320 A1 Apr. 27, 2017

(30) Foreign Application Priority Data
Jun. 27, 2014 (JP) .................................. 2014-132851

(51) Int. Cl.
*G06F 16/28* (2019.01)
*H04L 29/08* (2006.01)
(Continued)

(52) U.S. Cl.
CPC .......... *G06F 16/285* (2019.01); *A61B 5/4809* (2013.01); *G06F 11/3013* (2013.01);
(Continued)

(58) Field of Classification Search
CPC ...... H04L 67/306; H04L 67/22; H04W 4/023; H04W 4/21; H04W 4/029; G01C 21/3641;
(Continued)

(56) References Cited

U.S. PATENT DOCUMENTS 6,874,037 B1 * 3/2005 Abram ...................... H04L 7/10
709/248
8,082,243 B2 * 12/2011 Gorelik ............. G06F 16/24544
707/713
(Continued)

FOREIGN PATENT DOCUMENTS

| JP | 2011-096173 A | 5/2011 |
| JP | 2012-083676 A | 4/2012 |
| JP | 2013-164704 A | 8/2013 |

*Primary Examiner* — Dennis Truong
(74) *Attorney, Agent, or Firm* — Xsensus LLP

(57) ABSTRACT

[Object] To utilize various devices more effectively by organizing such devices. [Solution] Provided is an information processing apparatus including: a device log acquisition unit configured to acquire a device log including information indicating a state caused by behavior of a user related to each of devices from each of the devices; and a correlation determination unit configured to determine a correlation between certain devices included in the devices on the basis of the device logs and a preset condition of the states.

16 Claims, 14 Drawing Sheets

(51) Int. Cl.
*G06F 16/00* (2019.01)
*A61B 5/00* (2006.01)
*G06F 11/30* (2006.01)
*G06F 11/34* (2006.01)
*H04W 4/029* (2018.01)
*H04W 4/21* (2018.01)

(52) U.S. Cl.
CPC ...... *G06F 11/3438* (2013.01); *G06F 11/3476* (2013.01); *G06F 16/00* (2019.01); *H04L 67/22* (2013.01); *H04L 67/306* (2013.01); *H04W 4/029* (2018.02); *H04W 4/21* (2018.02)

(58) Field of Classification Search
CPC ............ G01C 21/3484; G01C 21/3617; G01C 21/367; G01C 21/362; G06F 16/285; G06F 16/35; G06F 16/48; G06F 1/163; G06F 3/013; G06F 11/3013; G06F 11/3438; G06F 11/3476; G06N 20/00; A61B 5/4809; G06K 9/00832; G06Q 30/0266; G06Q 30/0267; G08B 13/19647; G08B 21/0205; G08B 21/06; G08B 21/18; G08B 25/016; G08B 29/188; H04M 2203/2094; H04M 2250/02; H04M 2250/04
USPC ........... 707/737; 701/526; 702/1; 705/14.66; 706/46
See application file for complete search history.

(56) References Cited

U.S. PATENT DOCUMENTS

| | | | | |
|---|---|---|---|---|
| 8,510,247 B1* | 8/2013 | Kane, Jr. | .................. | G06N 5/02 706/46 |
| 9,073,505 B2* | 7/2015 | Hosokawa | .......... | B60R 21/0152 |
| 10,007,355 B2* | 6/2018 | Schorsch | ................ | G06F 3/017 |
| 10,110,435 B2* | 10/2018 | Palanciuc | ........... | H04L 41/0893 |
| 2007/0192038 A1* | 8/2007 | Kameyama | ........ | G01C 21/3641 702/19 |
| 2012/0041939 A1* | 2/2012 | Amsterdamski | ..... | G06F 16/9535 707/709 |
| 2013/0124309 A1* | 5/2013 | Traasdahl | ............. | G06F 9/5027 705/14.49 |
| 2013/0124331 A1* | 5/2013 | Doughty | ............ | G06Q 30/0269 705/14.66 |
| 2013/0238745 A1* | 9/2013 | Ramachandran | .. | H04N 21/2396 709/217 |
| 2014/0006954 A1* | 1/2014 | Raffa | ...................... | G06F 21/32 715/733 |
| 2014/0207489 A1* | 7/2014 | Wartena | ................. | G16H 15/00 705/3 |
| 2014/0244710 A1* | 8/2014 | Sharma | ................... | H04L 67/12 709/201 |
| 2014/0282877 A1* | 9/2014 | Mahaffey | ............ | H04L 63/0853 726/3 |
| 2014/0310594 A1* | 10/2014 | Ricci | ...................... | H04W 4/21 715/702 |
| 2015/0019131 A1* | 1/2015 | Basir | ...................... | G01C 21/26 701/526 |
| 2015/0019553 A1* | 1/2015 | Shaashua | ................ | H04W 4/70 707/737 |
| 2015/0089568 A1* | 3/2015 | Sprague | ................ | H04L 63/06 726/1 |
| 2015/0106198 A1* | 4/2015 | Miller | ................ | G06Q 30/0251 705/14.52 |
| 2015/0169891 A1* | 6/2015 | Hook | ...................... | G06F 16/23 726/29 |
| 2015/0324698 A1* | 11/2015 | Karaoguz | ............... | H04L 67/22 706/46 |
| 2015/0370814 A1* | 12/2015 | Liodden | ................ | G06F 16/955 707/738 |
| 2016/0224901 A1* | 8/2016 | Scarr | ..................... | H04W 4/029 |
| 2016/0337863 A1* | 11/2016 | Robinson | .............. | H04W 12/08 |
| 2018/0310121 A1* | 10/2018 | Milton | ................. | H04W 4/029 |

* cited by examiner

FIG.4A

| 220a | 220b | 220c | 220d | 220e | 220f |
|---|---|---|---|---|---|
| TIME | DEVICE ID | DEVICE TYPE | STATE | DETAILED STATE | POSITION |
| 2014/3/24 21:00:00 | 000001 | TV | VIDEO PLAYBACK | VIDEO TITLE : XXXXX | xxxxx,yyyyy (HOME) |
| 2014/3/24 21:00:00 | 000002 | SMARTPHONE | WEB BROWSING | WEB PAGE TITLE : XXXXX fan page | xxxxx,yyyyy (HOME) |

| 220a | 220b | 220c | 220d | 220e | 220f |
|---|---|---|---|---|---|
| TIME | DEVICE ID | DEVICE TYPE | STATE | DETAILED STATE | POSITION |
| 2014/3/24 21:00:00 | 000001 | TV | VIDEO PLAYBACK | VIDEO TITLE : XXXXX | xxxxx,yyyyy (HOME) |
| 2014/3/24 21:30:00 | 000001 | TV | — | — | xxxxx,yyyyy (HOME) |
| 2014/3/24 21:00:00 | 000003 | TABLET | — | — | xxxxx,yyyyy (HOME) |
| 2014/3/24 21:30:00 | 000003 | TABLET | VIDEO PLAYBACK | VIDEO TITLE : XXXXX | xxxxx,zzzzz |

| | TIME | DEVICE ID | DEVICE TYPE | STATE | DETAILED STATE | POSITION |
|---|---|---|---|---|---|---|
| | 220a | 220b | 220c | 220d | 220e | 220f |
| 220-7 | 2014/3/24 21:00:00 | 000001 | TV | VIDEO PLAYBACK | VIDEO TITLE : XXXXX | xxxxx,yyyyy (HOME) |
| 220-8 | 2014/3/24 21:00:00 | 000004 | SMARTPHONE | VIDEO PLAYBACK | VIDEO TITLE : YYYYY | xxxxx,yyyyy (HOME) |

FIG. 5

| | 240a | 240b | 240c | 240d | 240e | 240f | 240g |
|---|---|---|---|---|---|---|---|
| | STATE 1 | DETAILED STATE 1 | STATE 2 | DETAILED STATE 2 | TEMPORAL RELATIONSHIP | DETAILED CONDITION | CORRELATION |
| 240-1 | VIDEO PLAYBACK | {VIDEO TITLE} | WEB BROWSING | {WEB PAGE TITLE} | SYNCHRONIZATION | TITLES CORRESPOND TO EACH OTHER | YES |
| 240-2 | VIDEO PLAYBACK | {VIDEO TITLE} | VIDEO PLAYBACK | {VIDEO TITLE} | SWITCHOVER | TITLES CORRESPOND TO EACH OTHER | YES |
| 240-3 | VIDEO PLAYBACK | – | VIDEO PLAYBACK | – | SYNCHRONIZATION | – | NO |
| 240-4 | MUSIC PLAYBACK | – | MUSIC PLAYBACK | – | SYNCHRONIZATION | – | NO |
| 240-5 | USER MOVEMENT DETECTION | {MOVEMENT TRAJECTORY} | USER MOVEMENT DETECTION | {MOVEMENT TRAJECTORY} | SYNCHRONIZATION | MOVEMENT TRAJECTORIES ARE DIFFERENT | NO |
| 240-6 | GAME PLAY | {GAME TITLE} | WEB BROWSING | {WEB PAGE TITLE} | SYNCHRONIZATION | TITLES CORRESPOND TO EACH OTHER | YES |
| 240-7 | USER STATE DETECTION | DETECTION OF SLEEP | {ANY STATE} | DETECTION OF USER OPERATION | SYNCHRONIZATION | – | NO |
| 240-8 | ON | {DEVICE INSTALLATION SITE} | USER MOVEMENT DETECTION | {MOVEMENT TRAJECTORY} | SYNCHRONIZATION | END POINT OF MOVEMENT TRAJECTORY IS IN PROXIMITY TO INSTALLATION SITE | YES |
| 240-9 | OFF | {DEVICE INSTALLATION SITE} | USER MOVEMENT DETECTION | {MOVEMENT TRAJECTORY} | SYNCHRONIZATION | STARTING POINT OF MOVEMENT TRAJECTORY IS IN PROXIMITY TO INSTALLATION SITE | YES |
| 240-10 | ON | – | USER STATE DETECTION | DETECTION OF WAKING UP | SYNCHRONIZATION | – | YES |
| 240-11 | OFF | – | USER STATE DETECTION | DETECTION OF GOING TO BED | SYNCHRONIZATION | – | YES |
| 240-12 | KITCHEN APPLIANCE OPERATION DETECTION | {COOKING OPERATION TYPE} | WEB BROWSING | {WEB PAGE CONTENT} | SYNCHRONIZATION | RECIPE IN WEB PAGE CORRESPONDS TO COOKING OPERATION TYPE | YES |
| 240-13 | VEHICLE MOVEMENT DETECTION | {MOVEMENT TRAJECTORY} | NAVIGATION | {DESTINATION} | SYNCHRONIZATION | END POINT OF MOVEMENT TRAJECTORY IS IN PROXIMITY TO DESTINATION | YES |
| 240-14 | VEHICLE MOVEMENT DETECTION | {MOVEMENT DURATION} | USER STATE DETECTION | DETECTION OF SITTING | SYNCHRONIZATION | DURATION OF SITTING CORRESPONDS TO MOVEMENT DURATION | YES |

FIG.6

| | DEVICE ID-1 | DEVICE ID-2 | CORRELATION SCORE |
|---|---|---|---|
| 250-1 | 000001 | 000002 | +0.75 |
| 250-2 | 000001 | 000003 | +0.50 |
| 250-3 | 000001 | 000004 | -0.50 |

FIG.10

| GROUP ID | GROUP DETAIL | DEVICE ID |
|---|---|---|
| 500001 | 1-1-1 CHIYODA, CHIYODA-KU, TOKYO | 000007, 000015, 000036 |
| 500002 | 2-3-1 NAGATA-CHO, CHIYODA-KU, TOKYO | 000009, 000024 |

FIG.12

| | 220a | 220b | 220c | 220d | 220e | 220f |
|---|---|---|---|---|---|---|
| | TIME | DEVICE ID | DEVICE TYPE | STATE | DETAILED STATE | POSITION |
| 220-9 | 2014/1/1 10:00:00 | 000002 | SMARTPHONE | WEB BROWSING | WEB PAGE TITLE: XXXXX fan page | xxxxx,yyyyy (HOME) |
| 220-10 | 2014/1/1 10:00:00 | 000001 | TV | ON | - | xxxxx,yyyyy (HOME) |
| 220-11 | 2014/1/1 20:00:00 | 000005 | AIR CONDITIONER | ON | - | xxxxx,yyyyy (HOME) |

INFORMATION PROCESSING APPARATUS, INFORMATION PROCESSING METHOD, AND PROGRAM

CROSS REFERENCE TO RELATED APPLICATIONS

This application is a U.S. National Phase of International Patent Application No. PCT/JP2015/057944 filed on Mar. 17, 2015, which claims priority benefit of Japanese Patent Application No. JP 2014-132851 filed in the Japan Patent Office on Jun. 27, 2014. Each of the above-referenced applications is hereby incorporated herein by reference in its entirety.

TECHNICAL FIELD

The present invention relates to information processing apparatuses, information processing methods, and programs.

BACKGROUND ART

Patent Literature 1 discloses a technology for suppressing calculation cost to select an item by classifying users and items based on item use logs of the users. For example, many technologies for performing operation of aggregation, analysis, classification, or the like on data of a user specified by a user account, data of a log related to items registered in a database, or the like have already been proposed.

CITATION LIST

Patent Literature

Patent Literature 1: JP2013-164704A

SUMMARY OF INVENTION

Technical Problem

In recent years, various devices have intelligent functions. For example, not only information processing terminals such as a personal computer, a smartphone, and a tablet, various devices such as home appliances including an air conditioner, a refrigerator, and the like, a car, and a vending machine each of which includes a communication function, an information processing function, a sensing function, or the like, have become more and more popular. Such a device includes the communication function. However, unlike the information processing terminal, a user is not always identified by a login operation or the like. For example, like the vending machine, some device is configured to be used by many and unspecified users.

In a way similar to the information processing terminal, such a device can be used as a means for acquiring a device usage log and the like as statistical information of a user, or a means for outputting information to a user, for example. However, as described above, such a device does not identify a user (even in the case where the device is used by the specific user), or is configured to be used by many and unspecified users. Therefore, it is difficult to organize and use devices.

Accordingly, the present disclosure proposes a novel and improved information processing apparatus, information processing method, and program that are capable of utilizing various devices more effectively by organizing such devices.

Solution to Problem

According to the present disclosure, there is provided an information processing apparatus including: a device log acquisition unit configured to acquire a device log including information indicating a state caused by behavior of a user related to each of devices from each of the devices; and a correlation determination unit configured to determine a correlation between certain devices included in the devices on the basis of the device logs and a preset condition of the states.

According to the present disclosure, there is provided an information processing method including: acquiring a device log including information indicating a state caused by behavior of a user related to each of devices from each of the devices; and determining, by a processor, a correlation between certain devices included in the devices on the basis of the device logs and a preset condition of the states.

According to the present disclosure, there is provided a program for causing a computer to achieve: a function of determining a correlation between certain devices included in devices on the basis of a preset condition of a state caused by behavior of a user related to each of the devices, and a device log that has been acquired from each of the devices and that includes information indicating the state.

Advantageous Effects of Invention

As described above, according to the present disclosure, it is possible to utilize various devices more effectively by organizing such devices.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 4A is a diagram illustrating an example of a device log DB according to the first embodiment of the present disclosure.

FIG. 4B is a diagram illustrating an example of a device log DB according to the first embodiment of the present disclosure.

FIG. 4C is a diagram illustrating an example of a device log DB according to the first embodiment of the present disclosure.

FIG. 5 is a diagram illustrating an example of a correlation condition DB according to the first embodiment of the present disclosure.

FIG. 6 is a diagram illustrating an example of a correlation score DB according to the first embodiment of the present disclosure.

FIG. 10 is a diagram illustrating an example of a group DB according to the second embodiment of the present disclosure.

FIG. 12 is a diagram illustrating an example of a device log DB according to the third embodiment of the present disclosure.

DESCRIPTION OF EMBODIMENT(S)

Figure 1:
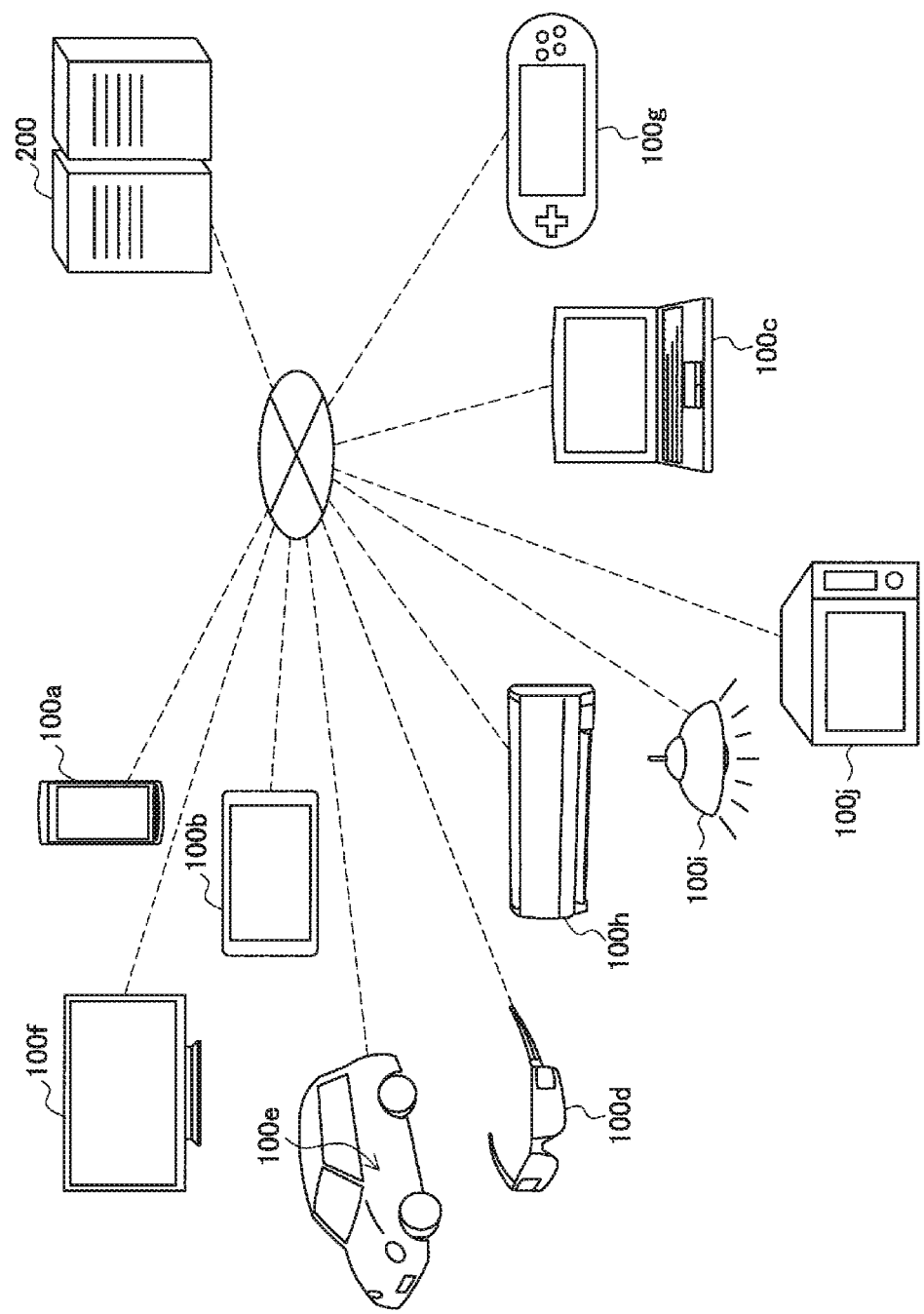
FIG. 1 is a diagram illustrating a schematic configuration of a system according to a first embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that the description is given in the following order.
1. First Embodiment
1-1. System configuration
1-2. Functional configuration of server
1-3. Workflow of process
1-4. Example of data
1-5. Specific example of correlation determination
2. Second Embodiment
3. Third Embodiment
4. Hardware Configuration
5. Supplement 1. First Embodiment 1-1. System Configuration FIG. 1 is a diagram illustrating a schematic configuration of a system according to a first embodiment of the present disclosure. With reference to FIG. 1, a system 10 according to the embodiment includes devices 100 and a server 200. As an example of the devices 100, FIG. 1 illustrates a smartphone 100*a*, a tablet 100*b*, a laptop personal computer (PC) 100*c*, a wearable device 100*d*, a car-mounted device 100*e*, a television 100*f*, a game console 100*g*, an air conditioner 100*h*, a light 100*i*, and a kitchen appliance 100*j*.

The example of the devices 100 is not limited thereto, and the devices 100 may include various other devices. For example, the devices 100 may include a mobile device other than the smartphone, tablet, and laptop PC. In addition to the illustrated eyewear, the devices 100 may include other wearable devices such as a contact lens type terminal, a watch type terminal, a bracelet type terminal, a ring type terminal, a headset, a terminal attached to clothing, a terminal integrated into clothing, a terminal attached to shoes, a terminal integrated into shoes, and a necklace type terminal. Specifically, the car-mounted device 100*e* may be a car navigation system or a rear seat entertainment system. The devices 100 are not limited to the television, game consoles, air conditioner, or light. The devices 100 may include every kind of consumer electronics (CE) devices having communication functions and information processing functions.

The devices 100 may include a device shared by many and unspecified users. For example, the devices 100 may include a public display, a terminal device used for an order system in a restaurant or the like, and a vending machine. In addition, sometimes the mobile device or the car-mounted device may be rented or mounted on a rental car, and used by many and unspecified users.

In the above described environment where there are various types of devices, one user often uses two or more of the devices 100. For example, the user may search for information on a movie by using the smartphone 100*a* during watching the movie on the television 100*f*. Alternatively, the user may ride on a vehicle equipped with the car-mounted device 100*e* while holding the tablet 100*b*. Alternatively, the user may switch on/off the air conditioner 100*h*, switch on/off the light 100*i*, or make a dish by using the kitchen appliance 100*j* while wearing the wearable device 100*d*. Alternatively, the user may search for walkthroughs of a game by using the laptop PC 100*c* while playing the game on the game console 100*g*.

In such cases, if it becomes possible to associate the two or more of the devices 100 with each other as devices 100 used by one user, such association helps acquiring various long-term logs of the user and helps selecting an optimum output device for providing the user with information, for example. However, such association of the devices 100 is possible only in a limited case, and in most cases it is difficult to associate the devices 100 with each other.

For example, when one user has logged in to services using the same user account via two or more of the devices 100, these devices 100 can be associated with each other. However, the devices 100 not always use the same user account. In addition, in a device 100 for using a service that does not require login or a device 100 without a function for performing a login operation, the user does not perform login at all.

On the other hand, for example, two or more devices 100 can be associated with each other in the case where these devices 100 identify users by analyzing images acquired by their cameras and the identified users are the same parson. However, the devices 100 do not always have the cameras, and the images of the user are not always acquired. In addition, the image analysis to identify a user requires high processing load, and it is difficult to enhance its accuracy.

On the other hand, for example, two or more devices 100 can be associated with each other in the case where network addresses such as IP addresses used for communication between these devices 100 are acquired and the network addresses are the same. In such a way, it is possible to associate devices 100 that are connected to each other via Wi-Fi or the like in a house, for example. However, a mobile device that performs communication via a mobile network such as a mobile telephone network even in the house has a different network address from a CE device that performs communication via a local area network (LAN) and a fixed line through a router. Therefore, it is difficult to associate the mobile device with the CE device.

According to the first embodiment (to be described later) of the present disclosure, for example, it is possible to easily evaluate a relation between devices 100 that are used by the same user by associating the devices 100 with each other in a way different from the above described examples.

1-2. Functional Configuration of Server

Figure 2:
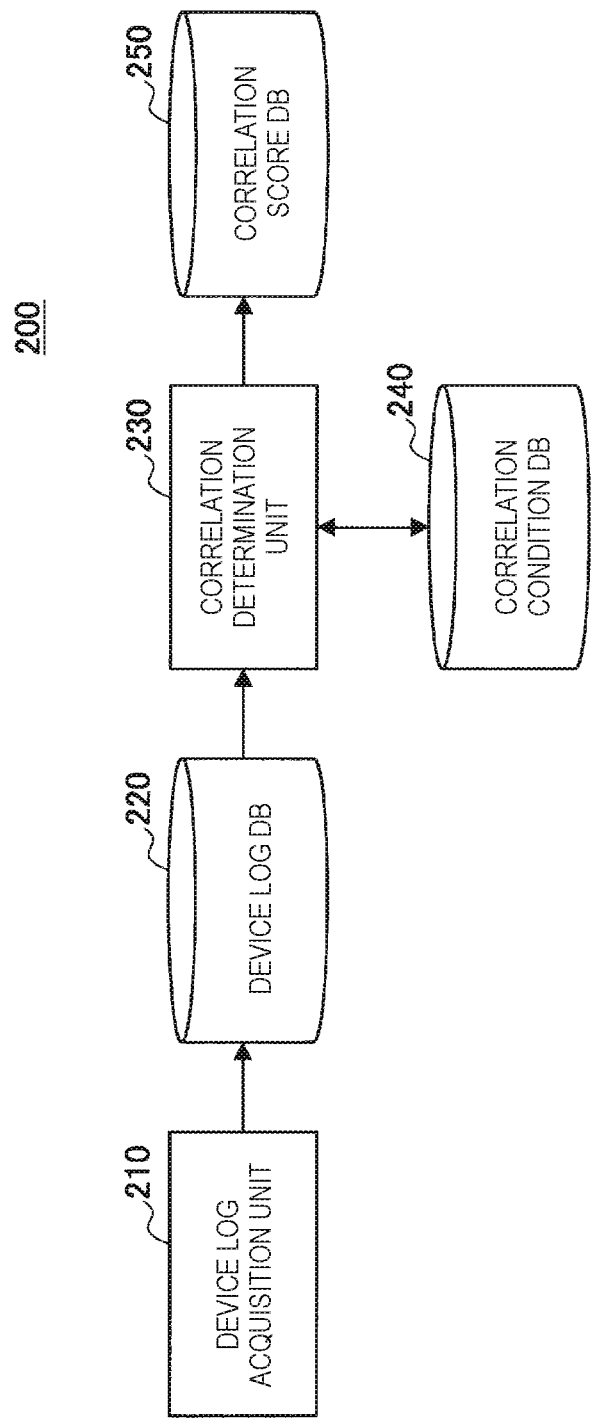
FIG. 2 is a block diagram schematically illustrating a functional configuration of a server according to an embodiment of the present disclosure.

FIG. 2 is a block diagram schematically illustrating a functional configuration of a server according to an embodiment of the present disclosure. With reference to FIG. 2, a server 200 includes a device log acquisition unit 210, a device log DB 220, a correlation determination unit 230, a correlation condition DB 240, and a correlation score DB 250.

The server 200 is realized by one or a plurality of server apparatuses on a network. Each of the server apparatuses is realized by a hardware configuration of an information processing apparatus (to be described later). For example, the device log acquisition unit 210 is realized by a communication apparatus, the device log DB 220, the correlation condition DB 240, and the correlation score DB 250 are realized by memory or a storage, and the correlation determination unit 230 is realized by a processor such as a CPU. In the case where the server 200 is realized by the plurality of server apparatus, each of the server apparatuses realizes one of the illustrated functional configurations. Alternatively, it is also possible that one functional configuration is distributed to the plurality of server apparatus.

The device log acquisition unit 210 acquires device logs provided by the devices 100 illustrated in FIG. 1. For example, the device log may be a log including information on a position of each device and information on a state caused by behavior of a user related to each device. For example, the device log acquisition unit 210 is transmitted from a device periodically or when a certain event occurs. In the embodiment, it is assumed that unique IDs (device ID and user ID) are assigned to the devices and users who use the devices. The logs acquired by the device log acquisition unit 21 are stored in the device log DB 220. A specific example of data stored in the device log DB 220 is described later.

The correlation determination unit 230 determines a correlation between at least two devices that provide the device logs. The correlation determination unit 230 determines a correlation between devices on the basis of preset conditions of states of the devices, and stores the result in the correlation score DB 250. The preset conditions are registered in the correlation condition DB 240. In the embodiment, the correlation condition DB 240 defines correlation conditions mainly in terms of whether or not respective devices are used by a same user. In the embodiment, a plus score is calculated for a combination of devices that are highly possible to have been used by a same user, and a minus score is calculated for a combination of devices that are highly possible to have been used by different users. A specific example of data stored in the correlation condition DB 240 and the correlation score DB 250 is described later.

1-3. Workflow of Process

Figure 3:
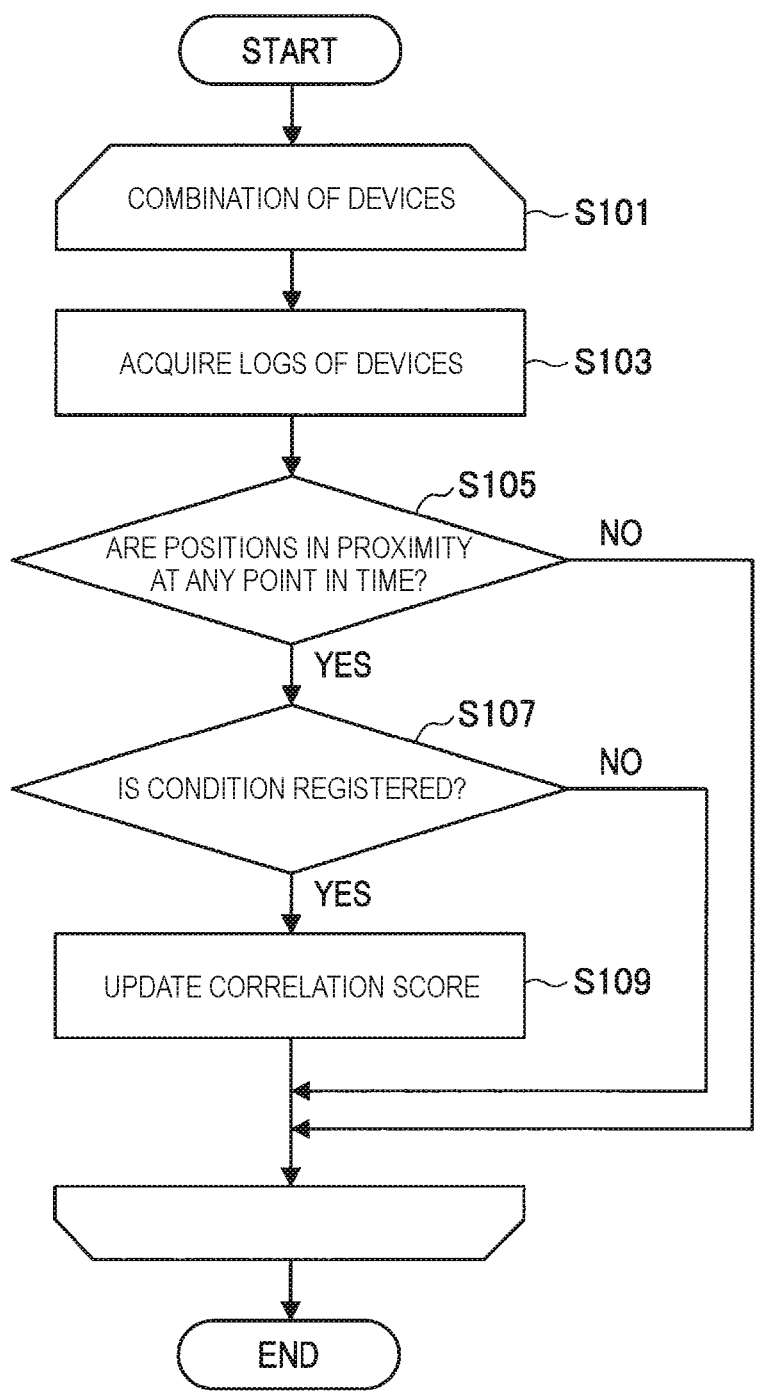
FIG. 3 is a flowchart illustrating an example of a process performed by a correlation determination unit according to the first embodiment of the present disclosure.

FIG. 3 is a flowchart illustrating an example of a process performed by the correlation determination unit according to the first embodiment of the present disclosure. With reference to FIG. 3, the correlation determination unit 230 first performs a loop process for each combination of devices on log data stored in the device log DB 220 (S101). Here, the correlation determination unit 230 acquires logs of the devices in the combination (S103). The acquired log may include a series of logs of each device that have been acquired in chronological order. It is assumed that the log includes at least time and positional information.

Next, the correlation determination unit 230 determines whether or not positions of the devices are in proximity at any point in time in accordance with the logs (S105), and calculates a correlation score in processes in subsequent Steps S107 to S109 only for a combination of devices that are in proximity at any point in time. Conversely, in the illustrated example, a correlation score is not calculated for a combination of devices that are not in proximity at every point in time. Such a combination of devices is treated as a combination for which it is impossible to determine whether or not devices are correlated (whether or not the devices have been used by a same user), for example. In addition, in this determination, it is only necessary that positions of devices are in proximity at least at a certain time. The positions may be different at a time other than the certain time.

In the case where it has been determined that the positions are in proximity at any point in time in the step S105, the correlation determination unit 230 further determines whether or not a condition indicated by logs of the devices is registered in the correlation condition DB 240 (S107). A specific example of the determination processes is described later in addition to a detailed example of the correlation condition DB 240. Here, in the case where it has been determined that the condition is not registered, a correlation score is not calculated in a way similar to the case where the positions are not in proximity, and the combination of the devices is treated as a combination for which it is impossible to determine whether or not devices are correlated (whether or not the devices have been used by a same user), for example.

In the case where it has been determined that the condition indicated by the logs of the devices is registered in the correlation condition DB 240 in the step S107, the correlation determination unit 230 updates the correlation score of the devices recorded in the correlation score DB 250, on the basis of information associated with the registered condition (S109). Here, as described later, correlation scores according to the embodiment include a positive score indicating a high correlation between devices and a negative score indicating a low correlation between devices. Accordingly, in the illustrated example, the correlation determination unit 230 determines level of a correlation of a combination of devices that are in proximity at least at any point in time, in accordance with the conditions registered in the correlation condition DB 240. On the other hand, the correlation determination unit 230 does not actively determine a correlation between devices other than the above described devices, that is, devices that are not in proximity at every point in time or devices that do not satisfy the conditions registered in the correlation condition DB 240.

1-4. Example of Data

FIG. 4A to FIG. 4C are each a diagram illustrating an example of the device log DB according to the first embodiment of the present disclosure. With reference to FIG. 4A to FIG. 4C, records in the device log DB 220 may include fields of time 220a, device ID 220b, device type 220c, state 220d, detailed state 220e, and position 220f. FIG. 4A to FIG. 4C will be referred to again for describing correlation determination in an example of the correlation condition DB 240 (to be described later).

The time 220a is a timestamp indicating time when a log has been acquired. The device ID 220b is an ID for identifying a device that has provided the log. The device type 220c is the type of the device that has provided the log (the device type may be separately defined in association with the device ID).

The state 220d is a state of the device indicated by the device ID 220b at the time 220a. With reference to the illustrated example, the state 220d may indicate a function of the device such as "video playback", "web browsing", or the like. Alternatively, the state 220d may indicate that the device has been switched on/off, simply indicate that the device has been operated, or indicate that the device has moved, for example.

The detailed state 220e indicates details of the state indicated by the state 220d. For example, like the illustrated example, the detailed state 220e may indicate the title of the video in the case where the state 220d is a "video playback" state. In the case where the state 220d is a "web browsing" state, the detailed state 220e may indicate the title of the web page.

The position 220f is a position of the device indicated by the device ID 220b at the time 220a. For example, the position 220f may be positional information acquired by each device providing positioning using a global navigation satellite system (GNSS) such as the GPS. Alternatively, the position 220f may be a position that the user has input in advance as a position where the device is fixedly installed (in this case, positional information provided by each device is a fixed value).

FIG. 5 is a diagram illustrating an example of the correlation condition DB according to the first embodiment of the present disclosure. With reference to FIG. 5, records in the correlation condition DB 240 may include fields of state (1) 240a, detailed state (1) 204b, state (2) 240c, detailed state (2) 240d, temporal relationship 240e, detailed condition 240f, and correlation 240g.

The states 240a and 240c designates states of devices in the combination of which a correlation is determined. For example, in the case where positions of two devices are in proximity at any point in time and one of the devices in the state 240a and the other of the devices is in the state 240c, it may be possible to determine a correlation between these devices.

With regard to the state 240a and 240c of the respective devices, the detailed states 240b and 240d designate information used in determination of the detailed condition 240f (to be described later). Therefore, depending on the detailed condition 240f, sometimes at least any of the detailed states 240b and 240d is not set. In addition, the detailed state 240b and 240b are not necessarily in proximity to the detailed state 220e in the device log DB 220.

The temporal relationship 240e indicates a temporal relationship between the states 240a and 240c of the respective devices. The illustrated example includes two types of the temporal relationship: "synchronization" and "switchover". The "synchronization" indicates that the states 240a and 240c of the devices are caused at the same time in parallel. The "switchover" indicates that the states 240a and 240c of the devices are caused alternately. A specific example of the temporal relationship will be described later.

The detailed condition 240f indicates an additional determination condition in the case where the states 240a and 240c are caused in the devices in the combination and the temporal relationship 240e is satisfied. For example, in a record 240-1, the detailed condition 240f is that, in the case where one of the devices is in the "video playback" state (state 240a) and the other of the devices is in the "web browsing" state (state 240c), the video title (detailed state 240b) of video played back in the "video playback" state corresponds to the web page title (detailed state 240d) of a web page browsed in the "web browsing state".

The correlation 240g indicates an estimated correlation between the devices in the combination in the case where a condition indicated in each record is satisfied. The illustrated example includes two types of the correlation: "YES" and "NO". "YES" indicates that the devices are highly possible to have been used by a same user, and a correlation between the device is high. "NO" indicates that the devices are highly possible to have been used by different users, and a correlation between the devices is low.

As described above, according to the embodiment, the correlation determination unit 230 estimates a correlation of devices in a combination indicated by the correlation 240g in the case where the condition defined in the correlation condition DB 240 is satisfied. In the case where the conditions are not satisfied, the correlation determination unit 230 does not estimate the correlation (according to the above example, the correlation determination unit 230 determines that the correlation is neither YES or NO).

FIG. 6 is a diagram illustrating an example of the correlation score DB according to the first embodiment of the present disclosure. With reference to FIG. 6, records in the correlation score DB 250 may include fields of device ID (1) 250a, device ID (2) 250b, and correlation score 250c.

According to the embodiment, the correlation determination unit 230 represents a correlation between devices determined in the above described process, as a correlation score. For example, the correlation determination unit 230 may add a predetermined correlation score with regard to a combination of devices in the case where a condition defined in a certain record in the correlation condition DB 240 are satisfied, and the correlation 240g of the certain record indicates that the correlation between the devices is high ("YES" in the example in FIG. 5). On the other hand, in the case where the correlation 240g indicates that the correlation between the devices is low ("NO" in the example in FIG. 5), the correlation determination unit 230 may subtract the predetermined correlation score with regard to the combination of the devices.

The device IDs 250a and 250b in the correlation score DB 250 of the illustrated example indicate devices in a combination for which a correlation score have been calculated. The correlation score 250c indicates a correlation score calculated for a combination of devices. For example, a record 250-1 indicates that a correlation score "+0.75" has been calculated for a combination of a device of ID "000001" and a device of ID "000002". Although this score is the positive correlation score like a record 250-2, the sore of the record 250-1 is higher than the record 250-2.

For example, in the case where a combination of certain devices satisfies a plurality of conditions defined in the correlation condition DB 240 and all the conditions indicate that the correlation between the certain devices is high, the correlation determination unit 230 may integrate correlation scores corresponding to the respective conditions with regard to the certain devices. In this case, the correlation score 250c becomes higher as the combination of devices satisfies more conditions (indicating that the correlation between the devices is high). Alternatively, the condition defined in the correlation condition DB 240 does not have to correspond to a binary correlation (YES or NO) as illustrated in FIG. 5, but may correspond to a gradual correlation according to strength of the estimated correlation. According to such a configuration, it is possible to represent a gradual correlation of each combination of devices in the embodiment.

On the other hand, a record 250-3 in the correlation score DB 250 of the illustrated example indicates that a correlation score "−0.50" has been calculated for a combination of the device of ID "000001" and a device of ID "000004". As described above, the negative correlation score is calculated in the case where the devices are highly possible to have been used by different users, and a correlation between the devices is low.

1-5. Specific Example of Correlation Determination

Next, with reference to the examples of a device log DB in FIG. 4A to FIG. 4C and the example of a correlation condition DB in FIG. 5, a specific example of correlation determination) according to the embodiment will be described.

As a first example, an example of two device (TV and smartphone) will be described with reference to FIG. 4A. Records 220-1 and 220-2 in the device log DB 220 illustrated in FIG. 4A indicate that the TV and the smartphone have been in the same position (home) at the same time (2014/3/24 21:00:00). Therefore, the combination of the TV and the smartphone in the records 220-1 and 220-2 goes through the determination in S105 in FIG. 3 and proceeds to determination based on the condition defined in the correlation condition DB 240.

At the above described time, the TV is in the "video playback" state, and the smartphone is in the "web browsing" state. Therefore, the states of these devices correspond to a "video playback" state 240a and a "web browsing" state 240c in the record 240-1 in the correlation condition DB 240 illustrated in FIG. 5. In addition, since the states of these devices are simultaneously caused at the above described time, the temporal relationship 240e "synchronization" in the record 240-1 is satisfied.

Subsequently, in order to determine whether a detailed condition 240f "titles correspond to each other" in the record 240-1 is satisfied, the correlation determination unit 230 acquires information recorded in detailed states 220e in the records 220-1 and 220-2. In the illustrated example, the detailed state 220e in the record 220-1 indicates that the title of the video that is being played back is "XXXXX". In addition, the detailed state 220e in the record 220-2 indicates that the title of the web page that is being browsed is "XXXXX fan page". For example, the correlation determination unit 230 checks whether character strings of the titles match with each other, and determines that the titles correspond to each other and the detailed condition 240f in the record 240-1 is satisfied.

As a result of the above described determination, as shown in the correlation 240g in the record 240-1, the correlation determination unit 230 estimates that it is highly possible that the TV and the smartphone of the records 220-1 and 220-2 are used by the same user and the correlation between the devices are high. The record 240-1 in the correlation condition DB 240 corresponds to the state in which the user is browsing information on the video by using a second device (smartphone here) while playing back the video on a first device (TV here), for example.

As described above, the correlation determination unit 230 determines that the correlation between the first device and the second device is high in the case where the first device provides the content of the first type, the second device provides the content of the second type that is different from the first type at the same time, and the content provided by these devices has a commonality. The combination of the types of the content is not limited to the video and the web page like the above described example. Combinations of any kinds of content are possible such as music content, a TV program, and an electronic book.

As a second example, an example of two device (TV and tablet) will be described with reference to FIG. 4B. Records 220-3 and 220-5 in the device log DB 220 illustrated in FIG. 4B indicate that the TV and the tablet have been in the same position (home) at the same time (2014/3/24 21:00:00). Therefore, the combination of the TV and the tablet in the records 220-3 to 220-6 goes through the determination in S105 in FIG. 3 and proceeds to determination based on the condition defined in the correlation condition DB 240.

The records 220-4 and 220-6 indicate that the devices are in different positions at another point in time (2014/3/24 21:30:00). However, as described above, it is only necessary that the devices are in proximity at any point in time in the determination in S105, the devices can be at different position at another point in time. Therefore, as described above, the combination of the TV and the tablet illustrated in FIG. 4B goes through the determination in S105 and proceeds to subsequent determination.

The record 220-3 indicates a state of the TV among the records 220-3 to 220-6. The record 220-3 indicates that the TV has been playing back the video at 21:00. The record 220-4 indicates that a state of the TV has not been detected at 21:30 (it may be possible that the TV has been powered off). On the other hand, the record 220-6 indicates a state of the tablet. The record 220-6 indicates that the tablet has been playing back the video at 21:30. The record 220-5 indicates that a state of the tablet has not been detected at 21:00 (it may be possible that the tablet has not provided any functions).

Since the TV is in the "video playback" state and the tablet is also in the "video playback" state in this case, it may be possible that the combination of the TV and the tablet in the records 220-3 and 220-6 satisfies a condition in a record 240-2 or 240-3 in the correlation condition DB 240 illustrated in FIG. 5. The temporal relationship 240e in the record 240-2 is "switchover". The "switchover" indicates that the states 240a and 240c of the devices are caused alternately. On the other hand, the temporal relationship 240e in the record 240-3 is "synchronization". The "video playback" state common in the records 220-3 and 220-6 has been caused in the TV at 21:00 and caused in the tablet at 21:30. Therefore, the temporal relationship 240e of "switchover" defined in the record 240-2 is satisfied.

Subsequently, in order to determine whether a detailed condition 240f "titles correspond to each other" in the record 240-2 is satisfied, the correlation determination unit 230 acquires information recorded in detailed states 220e in the records 220-3 and 220-6. In the illustrated example, the detailed state 220e in the record 220-3 indicates that the title of the video that has been played back is "XXXXX". In addition, the detailed state 220e in the record 220-6 indicates that the title of the video that has been played back is "XXXXX". For example, the correlation determination unit 230 checks whether character strings of the titles match with each other, and determines that the titles correspond to each other and the detailed condition 240f in the record 240-2 is satisfied.

As a result of the above described determination, as shown in the correlation 240g in the record 240-2, the correlation determination unit 230 estimates that it is highly possible that the TV and the tablet of the records 220-3 and 220-6 have been used by the same user and the correlation between the devices is high. The record 240-2 in the correlation condition DB 240 corresponds to the state in which a user has played back the video by using a first device (TV here), and the user has gone from one room to another room and has changed the first device to a second device (tablet here) to continue playback of the video, for example.

As described above, the correlation determination unit 230 determines that the correlation between the first device and the second device is high in the case where the first device provides the content of the first type, the second device provides the content of the first type alternately with the first device, and the content provided by these devices has a commonality. The types of the content are not limited to the video like the above described example. Any kinds of content is possible such as music content, a web page, a TV program, and an electronic book.

As a third example, an example of two devices (TV and smartphone) will be described with reference to FIG. 4C. Records 220-7 and 220-8 in the device log DB 220 illustrated in FIG. 4C indicate that the TV and the tablet have been in the same position (home) at the same time (2014/3/24 21:00:00). Therefore, the combination of the TV and the smartphone in the records 220-7 and 220-8 goes through the determination in S105 in FIG. 3 and proceeds to determination based on the condition defined in the correlation condition DB 240.

At the above described time, the TV is in the "video playback" state, and the smartphone is also in the "video playback" state. Therefore, it may be possible that the states of these devices correspond to a condition in a record 240-2 or the record 240-3 in the correlation condition DB 240 illustrated in FIG. 5. In addition, since the states of these devices have been simultaneously caused at the above described time, the temporal relationship 240e "switchover" in the record 240-2 is not satisfied but the temporal relationship 240e "synchronization" in the record 240-3 is satisfied.

In the record 240-3, the detailed condition 240f is not set. In other words, unlike the two examples described above, the condition defined in the record 240-3 is satisfied when the two devices (TV and smartphone) have been in the same position at the same time and are playing back video (titles of video do not matter). In this case, as shown in the correlation 240g in the record 240-3, the correlation determination unit 230 estimates that it is highly possible that the TV and the smartphone of the records 220-7 and 220-8 have been used by different users and the correlation between the devices is low. The record 240-3 in the correlation condition DB 240 corresponds to the state in which a first device (TV here) and a second device (smartphone here) are used by different users who are in proximity (for example, users live in the same house) to play back video, for example.

As described above, the correlation determination unit 230 determines that the correlation between the first device and the second device is low in the case where the first device provides the content of the first type, and the second device also provides content of the first type at the same time. The combination of the types of the content is not limited to the video and the web page like the above described example. Combinations of any kinds of content are possible such as music content, a TV program, and an electronic book.

Next, with reference to the other examples of the correlation condition DB illustrated in FIG. 5, the specific example of correlation estimation will be described.

In a way similar to the record 240-3 in the third example described above, the record 240-4 in the correlation condition DB 240 estimates that it is highly possible that two devices are used by different users and the correlation between the two devices is low in the case where the two devices are playing back music in synchronization. For example, the record 240-3 corresponds to a state in which a first device and a second device are used by different users who are in proximity to play back music. In a way similar to the records 240-3 and 240-4, the condition that the correlation between two devices is estimated to be low in the case where the two devices are playing back music in synchronization may be set with regard to content other than the video and the music.

A record 240-5 in the correlation condition DB 240 defines a condition that a correlation between two devices is estimated to be low if movement trajectories detected by the two devices are different in the case where the two devices detect movement of users at the same time by continuously acquiring positional information, for example. The devices moving along different movement trajectories at the same time are highly possible to have been used by different users.

A record 240-6 in the correlation condition DB 240 defines a condition that a correlation between two devices is estimated to be high if the title of a game that is being played with a first device corresponds to the title of a web page that is being browsed with a second device in the case where the first device provides a game function and the second device provides a web browsing function at the same time. In this case, for example, it is estimated that a user is playing the game with the first device (for example, game console) while referring to walkthroughs of the game with the second device (for example, tablet).

A record 240-7 in the correlation condition DB 240 defines a condition that a correlation between devices is estimated to be low if a second device (in any state) is detecting some user operation in the case where a first device is detecting that a state (behavior) of the user is a sleep state. When the devices are used by the same user, one device does not detect the user operation while the other device is detecting the sleep state.

A record 240-8 in the correlation condition DB 240 defines a condition that a correlation between two devices is estimated to be high when a second device (that is carried by a user and moves along with the user) finishes moving and an end point of the movement of the second device is in proximity to the installation site of a first device that has been fixedly installed in the case where the first device is turned on. For example, when a light or an air conditioner is turned on, a device moving toward the installation site of the light or the air conditioner is highly possible to have been carried or worn by a user arrived at the installation site (house, office, or the like).

A record 240-9 in the correlation condition DB 240 defines a condition that a correlation between two devices is estimated to be high when a second device (that is carried by a user and moves along with the user) starts moving and a starting point of the movement of the second device is in proximity to the installation site of a first device that has been fixedly installed in the case where the first device is turned off. For example, when a light or an air conditioner is turned off, a device starting to move away from the installation site of the light or the air conditioner is highly possible to have been carried or worn by a user left from the installation site (house, office, or the like).

A record 240-10 in the correlation condition DB 240 defines a condition that a correlation between devices is estimated to be high when a second device detects that a state (behavior) of a user is a wake-up state in the case where a first device is turned on. For example, if a user wakes up when the light or the air conditioner is turned on, it is highly possible that the light or the air conditioner in his/her home has been turned on by the user as behavior after waking up.

A record 240-11 in the correlation condition DB 240 defines a condition that a correlation between devices is estimated to be high when a second device detects that a user goes to bed as a state (behavior) of the user in the case where a first device is turned on. For example, if a user goes to bed when the light or the air conditioner is turned off, it is highly possible that the light or the air conditioner in his/her home has been turned off by the user as behavior before going to bed.

A record 240-12 in the correlation condition DB 240 defines a condition that a correlation between two devices is estimated to be high when a device (second device) is providing the web browsing function and a recipe in a web page corresponds to a type of operation of a kitchen appliance (first device), in the case where the operation on the kitchen appliance is detected. This condition also indicates that the second device provides an instruction (recipe) about user operation of a predetermined pattern in the case where the user operation of the predetermined pattern on the first device is detected. For example, it is highly possible that a smartphone and a microwave oven are used by the same user when the microwave oven starts heating for three minutes while the smartphone is displaying a web page of a recipe including a step "heating it in a microwave for three minutes".

A record 240-13 in the correlation condition DB 240 defines a condition that a correlation between devices is estimated to be high when a destination of navigation provided by a second device is in proximity to an end point of a moving trajectory in the case where a first device is detecting movement of a vehicle. For example, this condition is satisfied in the case where the first device is a car-mounted device, the second device is a smartphone, and a user uses the navigation in the smartphone while riding a car equipped with the car-mounted device.

A record 240-14 in the correlation condition DB 240 defines a condition that a correlation between devices is estimated to be high when a state of a user detected by a second device is a sitting state and duration of the sitting corresponds to duration of movement of a vehicle in the case where a first device detects the movement. In this case, sitting posture is posture of the user on a vehicle. According to the type or the state of the vehicle, standing posture or other posture may be detected. For example, a mobile device detects a sitting state of a user when a first device is a car-mounted device, a second device is the mobile device, and the user is traveling while sitting in a car equipped with the car-mounted device.

As described above, in the embodiment, the correlation condition DB 240 defines the conditions that a correlation between devices is estimated to be high or low. Therefore, a correlation between devices cannot be determined be high or low when the devices do not satisfy any condition defined in the correlation condition DB 240. The correlation determination unit 230 does not estimate a correlation between such devices and leaves it as it is. For example, the correlation cannot be determined to be high or low in the case where a first device detects that a state (behavior) of a user is an exercise state and a second device (in any state) detects user operation. This is because sometimes the user operates the device while exercising. Since the correlation in such a case is treated as "unknown" according to the embodiment, it is possible to prevent erroneous estimation and therefore it is possible to improve reliability of the estimation result.

In addition to the above described examples, there are various examples of the condition for estimating a correlation between devices. For example, a correlation between a public display and a mobile device is estimated to be high in the case where environment conditions such as temperature, humidity, brightness, and sound are satisfied, and the mobile device has detected that the user is in a stop state. Information indicating the environment conditions such as temperature, humidity, brightness, and sound is information indicating states caused by behavior of a user related to each device since the environment conditions change when the user goes to a specific place.

For example, when a correlation between a mobile device and a terminal device used for an order system in an restaurant or the like is estimated, the correlation between the mobile device and the terminal device is estimated to be high in the case where a picture of a menu ordered through the terminal device is posted on social media via the mobile device.

2. Second Embodiment

Next, a second embodiment of the present disclosure will be described. A schematic configuration of a system according to the embodiment is similar to the system 10 described with reference to FIG. 1. Therefore, repeated description is omitted.

Figure 7:
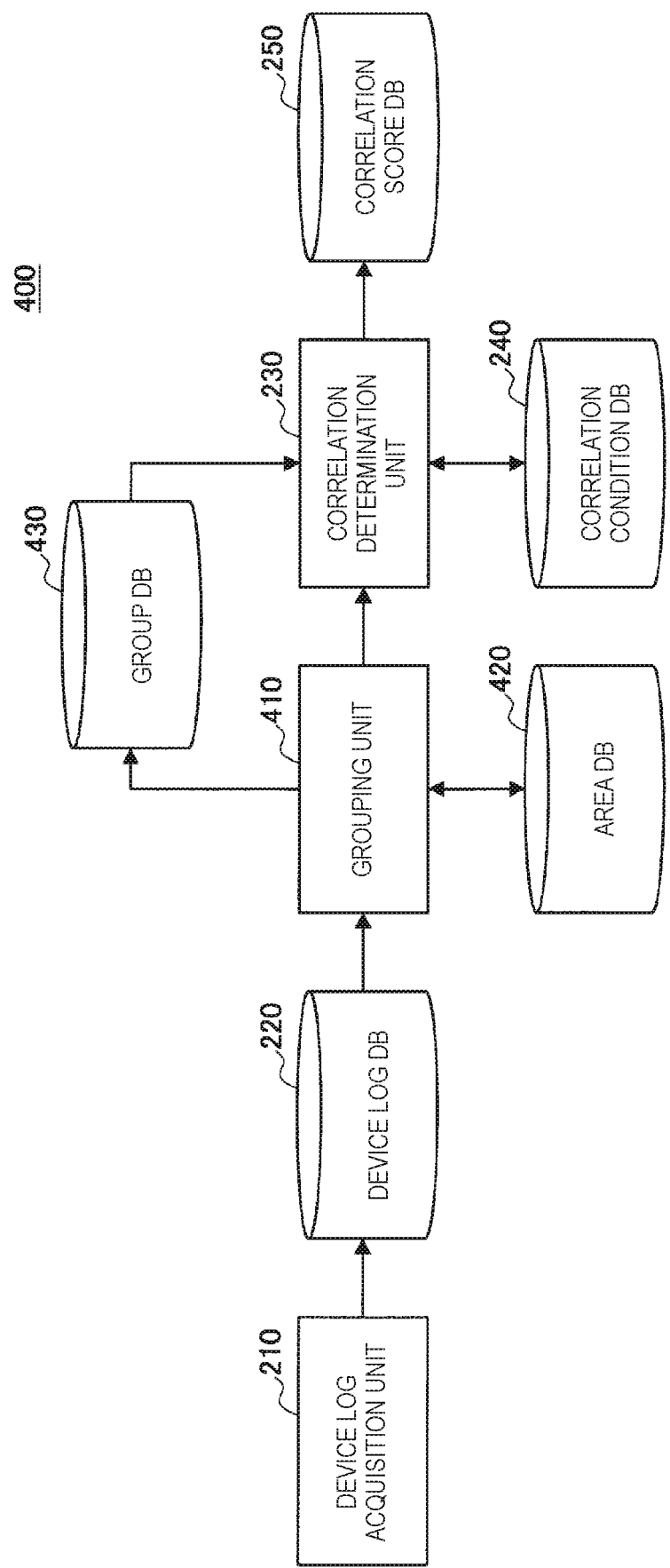
FIG. 7 is a block diagram schematically illustrating a functional configuration of a server according to a second embodiment of the present disclosure.

FIG. 7 is a block diagram schematically illustrating a functional configuration of a server according to the second embodiment of the present disclosure. With reference to FIG. 7, a server 400 includes the device log acquisition unit 210, the device log DB 220, the correlation determination unit 230, the correlation condition DB 240, the correlation score DB 250, a grouping unit 410, an area DB 420, and a group DB 430.

In a way similar to the server 200 according to the first embodiment, the server 400 is realized by one or a plurality of server apparatuses on a network. Each of the server apparatuses is realized by a hardware configuration of an information processing apparatus (to be described later). For example, the device log acquisition unit 210 is realized by a communication apparatus, the device log DB 220, the correlation condition DB 240, the correlation score DB 250, the area DB 420, and the group DB 430 are realized by memory or a storage, and the correlation determination unit 230 and the grouping unit 410 are realized by a processor such as a CPU. In the case where the server 400 is realized by the plurality of server apparatuses, each of the server apparatuses realizes one of the illustrated functional configurations. Alternatively, it is also possible that one functional configuration is distributed to the plurality of server apparatus.

Next, the functional configuration of the server 400 will be described. With regard to the device log acquisition unit 210, the device log DB 220, the correlation determination unit 230, the correlation condition DB 240, the correlation score DB 250, repeated description similar to the first embodiment is omitted.

The grouping unit 410 performs grouping on the devices 100 illustrated in FIG. 1 on the basis of data stored in the device log DB 220. More specifically, the grouping unit 410 performs grouping on the devices 100 on the basis of a relation between positions of the devices 100 indicated by logs stored in the device log DB 220, and a geographical area defined in the area DB 420 (positional conditions set in advance). For example, the area DB 420 defines areas corresponding to address areas. In this case, the grouping unit 410 converts positions of the devices 100 indicated by the logs or the like to addresses by using an external service or the like, and performs grouping on the devices 100 on the basis of the addresses. As the conversion from the positional information to the addresses, known technologies may be used such as JP 2008-89815A and JP 2011-43626A. The grouping unit 410 stores a result of the grouping in the group DB 430.

As described above, in the case where the devices 100 are subjected to the grouping process on the basis of the predefined areas, the grouping unit 410 performs grouping on the devices 100 under a condition that positions of the devices are in a common area at any point of time. The devices 100 that are in the common area at any point of time may be classified into the same group. In such a way, the grouping unit 410 classifies the devices into groups depending on areas.

In the embodiment, the correlation determination unit 230 determines a correlation between at least two devices that provide the device logs in a way similar to the first embodiment. However, in the server 400 according to the second embodiment, the correlation determination unit 230 refers to the group DB 430 and determines the correlation between the devices in the group. As described above, the group into which the devices are classified corresponds to the geographical area defined in the area DB 420, for example, the address area. The correlation determination unit 230 narrows down analysis targets to the devices in such a geographical area. Therefore, it is possible to reduce a calculation amount in comparison with the case where all the devices are treated as the analysis targets.

For example, in the case where the number of devices serving as the analysis targets is N and a relation between devices are determined for each combination of devices, calculation has to be performed $N^2$ times for all the combinations. Quadratic functional increase in the number of times of the calculation occurs as N increases. Therefore, in respect of reduction in the calculation amount, it is effective to limit the analysis targets to the devices in the same geographical area as described above.

Figure 8:
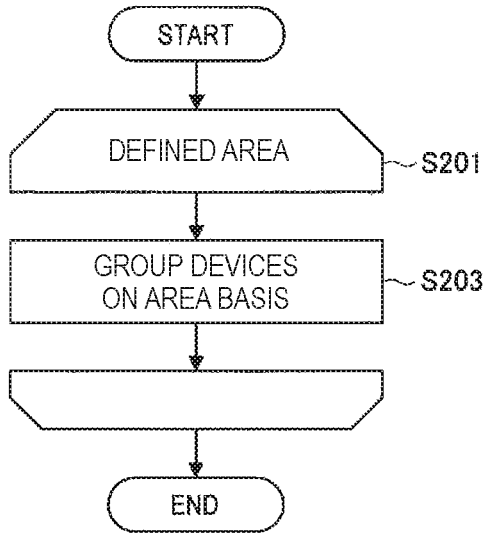
FIG. 8 is a flowchart illustrating an example of a grouping process performed on all devices according to the second embodiment of the present disclosure.

FIG. 8 is a flowchart illustrating an example of a grouping process performed on all devices according to the second embodiment of the present disclosure. With reference to FIG. 8, the grouping unit 410 performs a loop process for each area defined in the area DB 420 (S201), and groups devices on an area basis (S203). More specifically, for example, the grouping unit 410 groups the devices by checking whether an address area converted from the positional information of each device stored in the device log DB 220 matches with the address areas defined in the area DB 420.

A device in different positions according to time such as the mobile device may be included in a plurality of device groups of a plurality of areas. In this case, the positional information used for grouping the devices may be limited to information on a position where stay over a predetermined time has been detected.

The grouping unit 410 performs the grouping process on all the devices as an initial process or as batch processing performed periodically.

Figure 9:
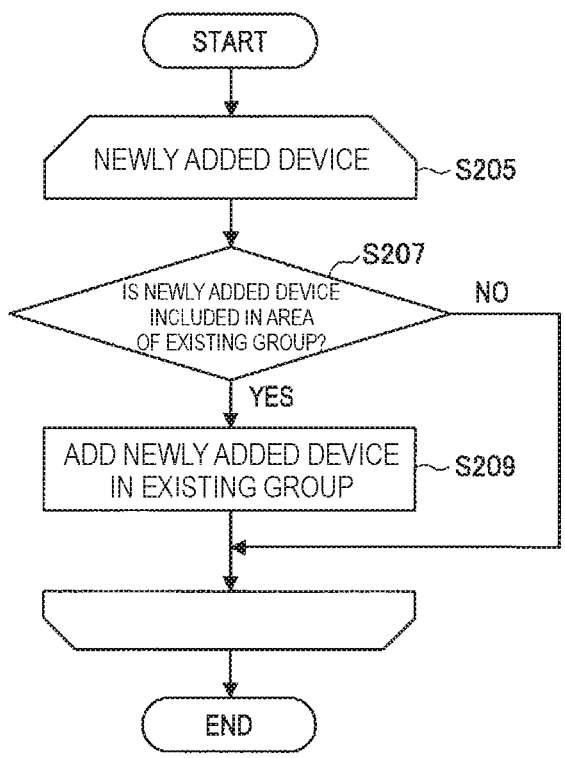
FIG. 9 is a flowchart illustrating an example of a grouping process performed on an additional device according to the second embodiment of the present disclosure.

FIG. 9 is a flowchart illustrating an example of a grouping process performed on an additional device according to the second embodiment of the present disclosure. With reference to FIG. 9, the grouping unit 410 performs a loop process for each device of which the device log acquisition unit 210 has newly acquired a log, in other words, for each device that has been newly added, for example (S205). Here, the grouping unit 410 determines whether or not the new device is included in the areas of the existing groups (S207). More specifically, for example, the grouping unit 410 checks whether an address area converted from the positional information of the new device matches with the address areas corresponding to the groups recorded in the group DB 430.

In the case where it has been determined that the new device is included in any of the areas of the existing groups (YES in S207), the grouping unit 410 adds the new device in the existing group (S209). On the other hand, in the case where the new device is not included in any of the areas of the existing groups (NO), the new device does not belong to any group in the illustrated example. In another example, the grouping unit 410 may additionally create a group including the new device in the case where the new device is not included in any of the areas of the existing groups.

The grouping unit 410 may perform the grouping process on the additional device periodically or every time a device is added after the grouping process illustrated in FIG. 9 is performed on all the devices at least once.

FIG. 10 is a diagram illustrating an example of the group DB according to the second embodiment of the present disclosure. With reference to FIG. 10, records in the group DB 430 may include fields of group ID 430a, group detail 430b, and device ID 430c.

The group ID 430a is an ID for identifying a group. The group ID 430a may be associated with an ID for defining an area in the area DB 420. The group detail 430b describes detailed information of a group. In the illustrated example, the group detail 430b describes an address of an address area corresponding to a group. The group detail 430b is not necessary in the case where there is other information associating the group ID with the area defined in the area DB 420. For example, the group detail 430b that describes the address may be used for notifying a user of a group to which a device belongs. The device ID 430c indicates the device that belongs to the group.

The means for recording a group to which each device belongs is not limited to the group DB 430 in the above example. For example, the device log DB 220 may record a group to which each device belongs at a time of acquiring a log. Alternatively, for example, the area DB 420 may record a device that belongs to a group corresponding to each area. Alternatively, a device DB may be provided in addition to the device log DB 220 to record a group to which each device belongs.

3. Third Embodiment

Next, a third embodiment of the present disclosure will be described. In the third embodiment, additional grouping is performed on a mobile device in addition to the grouping process according to the second embodiment. Configuration other than the additional grouping in the third embodiment is similar to the second embodiment. Therefore, repeated description will be omitted.

Figure 11:
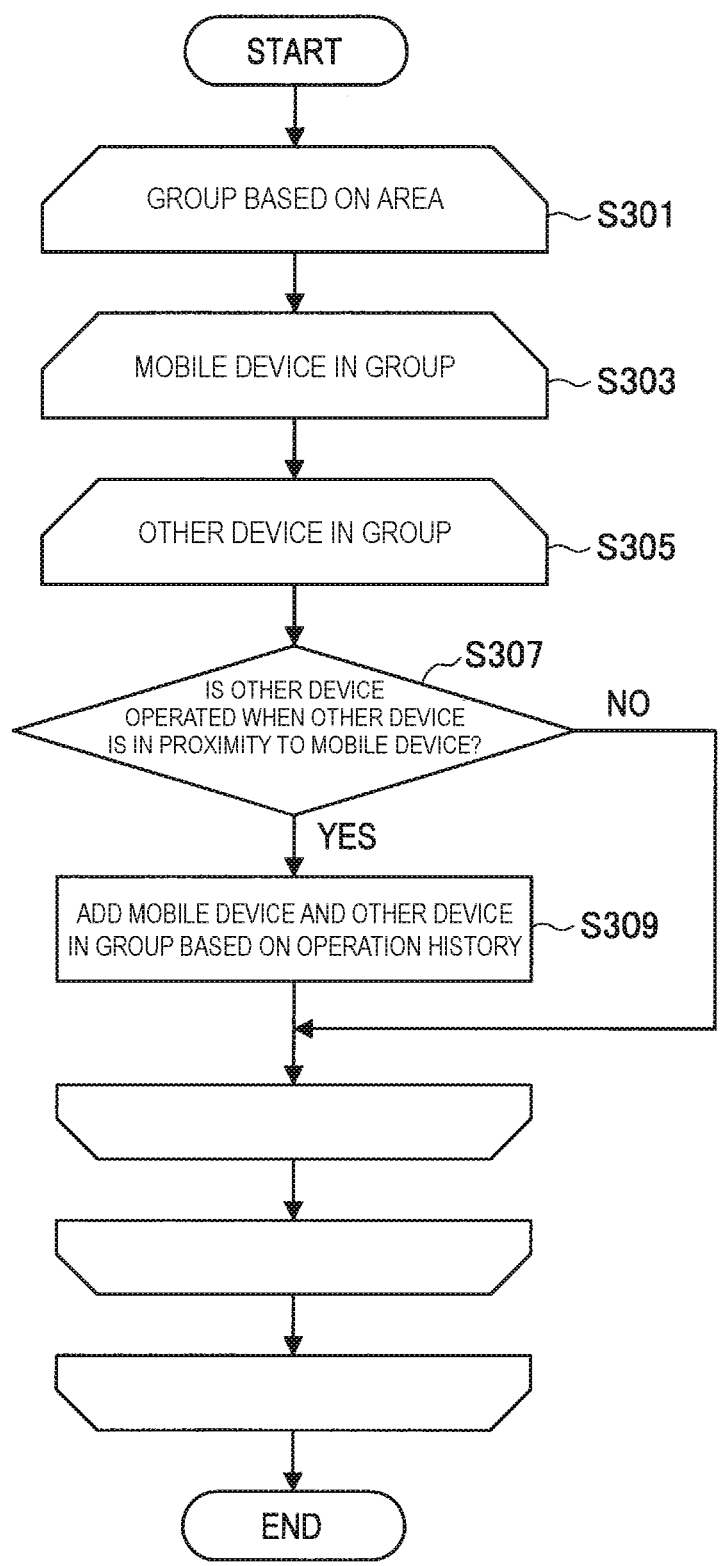
FIG. 11 is a flowchart illustrating an example of a grouping process according to a third embodiment of the present disclosure.

FIG. 11 is a flowchart illustrating an example of a grouping process according to the third embodiment of the present disclosure. With reference to FIG. 11, the grouping unit 410 performs a loop process for each group based on the area generated by a grouping process after the grouping process like the second embodiment is performed on all the devices at least once (S301). Here, the grouping unit 410 extracts mobile devices in each group and performs the loop process for each of the mobile devices (S303). In addition, the grouping unit 410 performs the loop process with the other device in the group for each of the mobile devices (S305).

In the loop process, the grouping unit 410 determines whether or not the other device is operated when proximity of the other device to the mobile device is detected (S307). More specifically, for example, the grouping unit 410 specifies time when the mobile device has come closer to the other device on the basis of the device log, and determines whether or not a user operation performed on the other device at that time is recorded in the device log. In the case where the other device is operated when the mobile device comes closer to the other device (YES), the grouping unit 410 adds the mobile device and the other device in a group based on an operation history (S309). The grouping unit 410 stores information on the group based on the operation history in the group DB 430.

According to the third embodiment, the group based on the operation history may be treated similar to the group based on the area according to the second embodiment. In other words, when determining a correlation between devices, the correlation determination unit 230 refers to the group DB 430 and determines the correlation between the devices in the group based on the operation history. The group based on the operation history may be coexistent with the group based on the area. According to the third embodiment, devices included in groups based on areas are further classified into subgroups based on operation histories according to a relation with each mobile device in the groups (sometimes one device belongs to a plurality of groups based on the operation histories). In the embodiment, a target of determination of a correlation between devices other than mobile devices may also be devices in a group based on an area, for example.

In the case where a correlation between the mobile device and the other devices is determined in terms of whether or not the mobile device and the other devices are used by the same user, it is unlikely that a device that is not operated when the device is in proximity to the mobile device that has been estimated to be carried by the user has a high correlation with the mobile device. Therefore, when determining the correlation with the mobile device, it is reasonable to limit an analysis area to a group based on the operation history. In the embodiment, the devices in the group based on the area are further classified into groups based on the operation histories. Thereby, it is possible to break down the group and reduce a calculation amount while maintaining an accuracy of determination.

FIG. 12 is a diagram illustrating an example of the device log DB according to the third embodiment of the present disclosure. With reference to FIG. 12, the device log DB 220 includes a record 220-9 of a smartphone, a record 220-10 of a TV, and a record 220-11 of an air conditioner.

The record 220-9 and record 220-10 indicate that the smartphone and the TV have been in proximity at a certain point of time (2014/1/1 10:00) (the smartphone and the TV are in home), and the TV has been operated (turned on) at that time. In this case, the grouping unit 410 according to the embodiment may perform a process to classify the smartphone (mobile device) in the record 220-9 and the TV (another device) in the record 220-10 into the same group on an operation history basis.

On the other hand, the record 220-9 and the record 220-11 indicate that although the smart phone and the air conditioner have been in proximity (the air conditioner has been estimated to be in the home at 2014/1/1 10:00 since the air conditioner has been fixedly installed), the air conditioner has not been operated at that time and the air conditioner has been operated (turned on) after the smartphone has gotten away from the air conditioner. In this case, the grouping unit 410 according to the embodiment does not perform a process to classify the smartphone (mobile device) in the record 220-9 and the air conditioner (another device) in the record 220-11 into the same group on an operation history basis.

Modification

In the above described embodiments, the devices that has classified into groups on an area basis are further subjected to grouping on an operation history basis. However, in another example, all devices may be subjected to grouping on an operation history basis before the devices are classified into groups on the area basis. In this case, the devices are first subjected to grouping based on a relation with each mobile device. For example, in the case where a TV in a home and a PC in an office are operated when a common mobile device comes closer to the TV or the PC, the TV and the PC may be classified into a same group. In addition, as necessary, the group on an operation history basis may be broken down into subgroups on an area basis.

According to the first to third embodiments of the present disclosure, it is possible to estimate a correlation between various devices such as a mobile device, a wearable device, a car-mounted device, and a CE device. In addition, by organizing the devices according to their correlations, it is possible to acquire more detailed profile of preference and behavior patterns of users, and it is possible to select an optimum device to present information to a user.

In addition, for example, when a correlation between a device shared by many and unspecified users such as a public display and a device dedicated to an individual user such as a mobile device is estimated, it is possible to individually track effects of information (for example, advertisement) provided by the shared device on behavior of the user. In addition, for example, information output via the shared device may be changed according to the user in the case where the shared device is temporally occupied by the user or in the case where it is estimated that a rate of the number of users having a specific attribute among the users using the shared device is high.

In the first to third embodiments, the correlation is estimated in terms of whether or not the devices are used by the same user. However, the embodiments of the present disclosure are not limited thereto. For example, the correlation between the devices may be estimated in terms of whether or not the devices are used by users having the same attribute such as age, job, or sex. In addition, the grouping process according to the second and third embodiments is not limited to the case of determining a correlation between devices. The grouping process may be useful for reducing a calculation amount also in any case of analyzing a correlation of a combination of certain devices in a device group. In this respect, it can be said that the correlation determination unit 230 according to the above described embodiments is a relation analysis unit that analyzes a relation between devices on the basis of device logs.

4. Hardware Configuration

Figure 13:
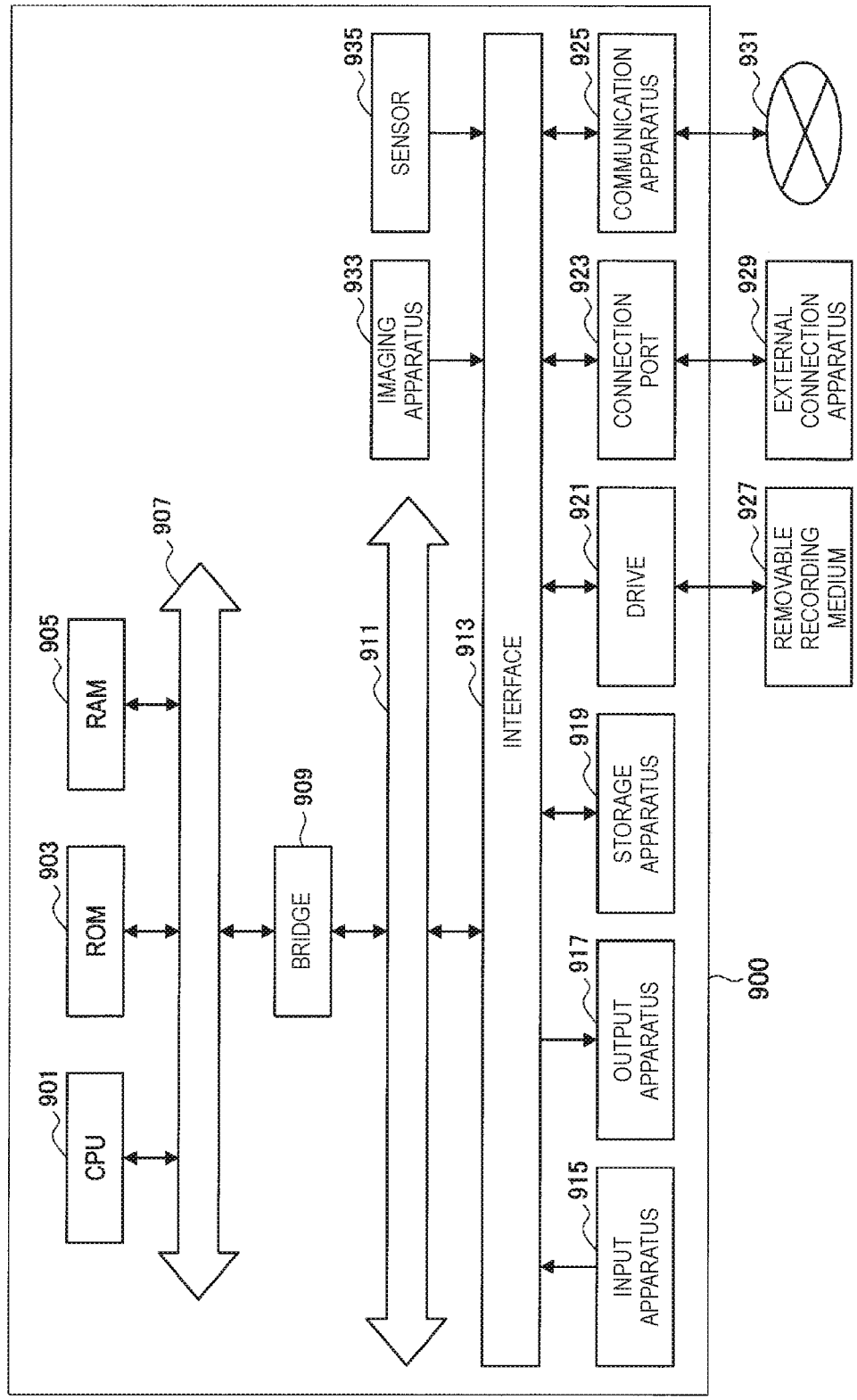
FIG. 13 is a block diagram illustrating a hardware configuration example of an information processing apparatus according to an embodiment of the present disclosure.

Next, with reference to FIG. 13, a hardware configuration of an information processing apparatus according to an embodiment of the present disclosure is explained. FIG. 13 is a block diagram illustrating a hardware configuration example of an information processing apparatus according to the embodiment of the present disclosure. An illustrated information processing apparatus 900 may achieve the server apparatus according to the embodiments of the present disclosure, for example.

The information processing apparatus 900 includes a central processing unit (CPU) 901, read only memory (ROM) 903, and random access memory (RAM) 905. In addition, the information processing apparatus 900 may include a host bus 907, a bridge 909, an external bus 911, an interface 913, an input apparatus 915, an output apparatus 917, a storage apparatus 919, a drive 921, a connection port 923, and a communication apparatus 925. Moreover, the information processing apparatus 900 may include an imaging apparatus 933, and a sensor 935, as necessary. The information processing apparatus 900 may include a processing circuit such as a digital signal processor (DSP), an application-specific integrated circuit (ASIC), or a field-programmable gate array (FPGA), alternatively or in addition to the CPU 901.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 transiently stores programs used when the CPU 901 is executed, and various parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input apparatus 915 is a device operated by a user such as a mouse, a keyboard, a touch panel, a button, a switch, and a lever. The input apparatus 915 may be a remote control device that uses, for example, infrared radiation and another type of radiowave. Alternatively, the input apparatus 915 may be an external connection apparatus 929 such as a mobile phone that corresponds to an operation of the information processing apparatus 900. The input apparatus 915 includes an input control circuit that generates input signals on the basis of information which is input by a user to output the generated input signals to the CPU 901. A user inputs various types of data to the information processing apparatus 900 and instructs the information processing apparatus 900 to perform a processing operation by operating the input apparatus 915.

The output apparatus 917 includes an apparatus that can report acquired information to a user visually, audibly, or haptically. The output apparatus 917 may be, for example, a display device such as a liquid crystal display (LCD) or an organic electro-luminescence (EL) display, an audio output apparatus such as a speaker or a headphone, or a vibrator. The output apparatus 917 outputs a result obtained through a process performed by the information processing apparatus 900, in the form of video such as text and an image, sounds such as voice and audio sounds, or vibration.

The storage apparatus 919 is an apparatus for data storage that is an example of a storage unit of the information processing apparatus 900. The storage apparatus 919 includes, for example, a magnetic storage device such as a hard disk drive (HDD), a semiconductor storage device, an optical storage device, or a magneto-optical storage device.

The storage apparatus 919 stores therein the programs and various data executed by the CPU 901, various data acquired from an outside, and the like.

The drive 921 is a reader/writer for the removable recording medium 927 such as a magnetic disk, an optical disc, a magneto-optical disk, and a semiconductor memory, and built in or externally attached to the information processing apparatus 900. The drive 921 reads out information recorded on the mounted removable recording medium 927, and outputs the information to the RAM 905. The drive 921 writes the record into the mounted removable recording medium 927.

The connection port 923 is a port used to connect devices to the information processing apparatus 900. The connection port 923 may include a Universal Serial Bus (USB) port, an IEEE1394 port, and a Small Computer System Interface (SCSI) port. The connection port 923 may further include an RS-232C port, an optical audio terminal, a High-Definition Multimedia Interface (HDMI) (registered trademark) port, and so on. The connection of the external connection device 929 to the connection port 923 makes it possible to exchange various data between the information processing apparatus 900 and the external connection device 929.

The communication apparatus 925 is a communication interface including, for example, a communication device for connection to a communication network 931. The communication apparatus 925 may be, for example, a communication card for a local area network (LAN), Bluetooth (registered trademark), Wi-Fi, or a wireless USB (WUSB). The communication apparatus 925 may also be, for example, a router for optical communication, a router for asymmetric digital subscriber line (ADSL), or a modem for various types of communication. For example, the communication apparatus 925 transmits and receives signals in the Internet or transits signals to and receives signals from another communication device by using a predetermined protocol such as TCP/IP. The communication network 931 to which the communication apparatus 925 connects is a network established through wired or wireless connection. The communication network 931 may include, for example, the Internet, a home LAN, infrared communication, radio communication, or satellite communication.

The imaging apparatus 933 is an apparatus that captures an image of a real space by using an image sensor such as a charge coupled device (CCD) and a complementary metal oxide semiconductor (CMOS), and various members such as a lens for controlling image formation of a subject image onto the image sensor, and generates the captured image. The imaging apparatus 933 may capture a still image or a moving image.

The sensor 935 is various sensors such as an acceleration sensor, an angular velocity sensor, a geomagnetic sensor, an illuminance sensor, a temperature sensor, a barometric sensor, and a sound sensor (microphone). The sensor 935 acquires information regarding a state of the information processing apparatus 900 such as a posture of a housing of the information processing apparatus 900, and information regarding an environment surrounding the information processing apparatus 900 such as luminous intensity and noise around the information processing apparatus 900. The sensor 935 may include a global positioning system (GPS) receiver that receives GPS signals to measure latitude, longitude, and altitude of the apparatus.

The example of the hardware configuration of the information processing apparatus 900 has been described. Each of the structural elements described above may be configured by using a general purpose component or may be configured by hardware specialized for the function of each of the structural elements. The configuration may be changed as necessary in accordance with the state of the art at the time of working of the present disclosure.

5. Supplement

The embodiments of the present disclosure may include, for example, the above-described information processing apparatus (for example, server), the above-described system, the information processing method executed by the information processing apparatus or the system, a program for causing the information processing apparatus to exhibits its function, and a non-transitory physical medium having the program stored therein.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)

An information processing apparatus including:

a device log acquisition unit configured to acquire a device log including information indicating a state caused by behavior of a user related to each of devices from each of the devices; and a correlation determination unit configured to determine a correlation between certain devices included in the devices on the basis of the device logs and a preset condition of the states.

(2)

The information processing apparatus according to (1), wherein the devices include a first device and a second device, and the condition includes a first condition that a first state of the first device and a second state of the second device are caused in parallel.

(3)

The information processing apparatus according to (2), wherein the device logs further include information indicating positions of the first device and the second device, the correlation determination unit determines that the first device and the second device have a high correlation in a case where the position of the first device and the position of the second device are in proximity at least at any point in time while the first state and the second state are caused in parallel.

(4)

The information processing apparatus according to (3), wherein the first state indicates that the first device provides content of a first type, the second state indicates that the second device provides content of a second type that is different from the first type, and the first condition further includes a condition that the content of the first type and the content of the second type have a commonality.

(5)

The information processing apparatus according to (3), wherein the first state indicates that the first device is switched on, the second state indicates that the second device finishes moving, and the first condition further includes a condition that an end point of the movement of the second device is in proximity to an installation site of the first device.

(6)

The information processing apparatus according to (3), wherein the first state indicates that the first device is switched off, the second state indicates that the second device starts moving, and the first condition further includes a condition that a starting point of the movement of the second device is in proximity to an installation site of the first device.

(7)

The information processing apparatus according to (3), wherein the first state indicates that the first device is switched on, and the second state indicates that the second device detects that the user wakes up.

(8)

The information processing apparatus according to (3), wherein the first state indicates that the first device is switched off, the second state indicates that the second device detects that the user goes to bed.

(9)

The information processing apparatus according to (3), wherein the first state indicates a user operation of a predetermined pattern on the first device, and the second state indicates that the second device provides an instruction of the user operation of the predetermined pattern.

(10)

The information processing apparatus according to (3), wherein the first state indicates movement of a vehicle equipped with the first device, the second state indicates that the second device provides navigation of the vehicle, and the first condition further includes a condition that an end point of the movement of the vehicle is in proximity to a destination of the navigation.

(11)

The information processing apparatus according to (3), wherein the first state indicates movement of a vehicle equipped with the first device, the second state indicates that the second device detects posture of the user in the vehicle, and the first condition further indicates that movement duration of the vehicle corresponds to duration of the posture.

(12)

The information processing apparatus according to (2), wherein the device log further includes information indicating positions of the first device and the second device, and the correlation determination unit determines that the first device and the second device have a low correlation in a case where the position of the first device and the position of the second device are in proximity at least at any point in time while the first state and the second state are caused in parallel.

(13)

The information processing apparatus according to (12), wherein the first state indicates that the first device provides content of a first type, and the second state indicates that the second device also provides content of the first type.

(14)

The information processing apparatus according to (12), wherein the first state indicates that the first device detects sleep of the user, and the second state indicates that some operation is performed on the second device.

(15)

The information processing apparatus according to any one of (1) to (14), wherein the devices include a first device and a second device, and the condition includes a second condition that a third state of the first device and a fourth state of the second device are caused alternately.

(16)

The information processing apparatus according to (15), wherein the device log further includes information indicating positions of the first device and the second device, and the correlation determination unit determines that the first device and the second device have a high correlation in a case where the position of the first device and the position of the second device are in proximity at least at any point in time while the third state and the fourth state are caused alternately.

(17)

The information processing apparatus according to (16), wherein the third state indicates that the first device provides content of a first type, the fourth state indicates that the second device also provides content of the first type, and the second condition further includes a condition that the content provided by the first device and the content provided by the second device have a commonality.

(18)

An information processing method including:

acquiring a device log including information indicating a state caused by behavior of a user related to each of devices from each of the devices; and determining, by a processor, a correlation between certain devices included in the devices on the basis of the device logs and a preset condition of the states.

(19)

A program for causing a computer to achieve:

a function of determining a correlation between certain devices included in devices on the basis of a preset condition of a state caused by behavior of a user related to each of the devices, and a device log that has been acquired from each of the devices and that includes information indicating the state.

REFERENCE SIGNS LIST

10 system
100 device
200, 400 server
210 device log acquisition unit
220 device log DB
230 correlation determination unit
240 correlation condition DB
250 correlation score DB
410 grouping unit
420 area DB
430 group DB

The invention claimed is:

1. An information processing apparatus comprising circuitry configured to:

acquire a device log comprising information indicating a state caused by behavior of a user related to each of a first device and a second device; and calculate a correlation score between the first device and the second device on the basis of the device log, wherein the correlation score indicates a possibility that the first device and the second device are used by a same user, and the correlation score indicates that the possibility is higher when the circuitry determines that the first device is in a first state at a same time as the second device is in a second state different from the first state, wherein the first state comprises providing first content of a first type and the second state comprises providing second content of a second type different from the first type, wherein the correlation score indicates that the possibility is higher when the circuitry determines that the first content has a commonality with the second content, and wherein the circuitry determines that the commonality exists when a first title of the first content at least partially matches a second title of the second content.

2. The information processing apparatus according to claim 1, wherein the device log further comprises information indicating a first position of the first device and a second position of the second device, the circuitry is further configured to determine that the first device and the second device have a high correlation in a case where the first position of the first device and the second position of the second device are in proximity at least at any point in time while the first state and the second state are caused in parallel.

3. The information processing apparatus according to claim 2, wherein the first state indicates that the first device is switched on, the second state indicates that the second device finishes moving, and the correlation score indicates that the possibility is higher when an end point of the movement of the second device is in proximity to an installation site of the first device.

4. The information processing apparatus according to claim 2, wherein the first state indicates that the first device is switched off, the second state indicates that the second device starts moving, and the correlation score indicates that the possibility is higher when a starting point of the movement of the second device is in proximity to an installation site of the first device.

5. The information processing apparatus according to claim 2, wherein the first state indicates that the first device is switched on, and the second state indicates that the second device detects that the user wakes up.

6. The information processing apparatus according to claim 2, wherein
the first state indicates that the first device is switched off,
the second state indicates that the second device detects that the user goes to bed.

7. The information processing apparatus according to claim 2, wherein
the first state indicates a user operation of a predetermined pattern on the first device, and
the second state indicates that the second device provides an instruction of the user operation of the predetermined pattern.

8. The information processing apparatus according to claim 2, wherein
the first state indicates movement of a vehicle equipped with the first device,
the second state indicates that the second device provides navigation of the vehicle, and
the correlation score indicates that the possibility is higher when Id point of the movement of the vehicle is in proximity to a destination of the navigation.

9. The information processing apparatus according to claim 2, wherein
the first state indicates movement of a vehicle equipped with the first device,
the second state indicates that the second device detects a posture of the user in the vehicle, and
the correlation score indicates that the possibility is higher when a movement duration of the vehicle corresponds to a duration of the posture.

10. The information processing apparatus according to claim 1, wherein
the device log further includes information indicating a first position of the first device and a second position of the second device, and
the circuitry is further configured to determine that the first device and the second device have a low correlation in a case where the first position of the first device and the second position of the second device are in proximity at least at any point in time while the first state and the second state are caused in parallel.

11. The information processing apparatus according to claim 1, wherein the circuitry is further configured to calculate the correlation score based on a second condition that a third state of the first device and a fourth state of the second device are caused alternately.

12. The information processing apparatus according to claim 11, wherein
the device log further includes information indicating a first position of the first device and a second position of the second device, and
the circuitry is further configured to determine that the first device and the second device have a high correlation in a case where the first position of the first device and the second position of the second device are in proximity at least at any point in time while the third state and the fourth state are caused alternately.

13. The information processing apparatus according to claim 12, wherein
the third state indicates that the first device provides content of a first type,
the fourth state indicates that the second device also provides content of the first type, and
the second condition further includes a condition that the content provided by the first device and the content provided by the second device have a commonality.

14. The information processing apparatus according to claim 1, wherein the correlation score is calculated in response to a determination that the first device has been in proximity to the second device.

15. An information processing method comprising:
acquiring a device log including information indicating a state caused by behavior of a user related to each of a first device and a second device; and
calculating, by a processor, a correlation score between the first device and the second device on the basis of the device log,
wherein the correlation score indicates a possibility that the first device and the second device are used by a same user, and the correlation score indicates that the possibility is higher when it is determined that the first device is in a first state at a same time as the second device is in a second state different from the first state,
wherein the first state comprises providing first content of a first type and the second state comprises providing second content of a second type different from the first type,
wherein the correlation score indicates that the possibility is higher when it is determined that the first content has a commonality with the second content, and
wherein it is determined that the commonality exists when a first title of the first content at least partially matches a second title of the second content.

16. A non-transitory computer readable medium comprising a program for causing a computer to:
calculate a correlation score between a plurality of devices on the basis of a preset condition of a state caused by behavior of a user related to each of the devices, and a device log that has been acquired from each of the devices and that includes information indicating the state,
wherein the correlation score indicates a possibility that the first device and the second device are used by a same user, and the correlation score indicates that the possibility is higher when it is determined that the first device is in a first state at a same time as the second device is in a second state different from the first state,
wherein the first state comprises providing first content of a first type and the second state comprises providing second content of a second type different from the first type,
wherein the correlation score indicates that the possibility is higher when it is determined that the first content has a commonality with the second content, and
wherein it is determined that the commonality exists when a first title of the first content at least partially matches a second title of the second content.

* * * * *